US005684025A

United States Patent [19]

Tsao et al.

[11] Patent Number: 5,684,025

[45] Date of Patent: Nov. 4, 1997

[54] LIQUID FORMULATIONS OF 1,2-BENZISOTHIAZOLIN-3-ONE

[75] Inventors: Techen Tsao, Highland Park; Jeffery S. Hinkle, Franklin Park, both of N.J.

[73] Assignee: Huls America Inc., Somerset, N.J.

[21] Appl. No.: 715,395

[22] Filed: Sep. 13, 1996

Related U.S. Application Data

[62] Division of Ser. No. 505,013, Jul. 21, 1995, Pat. No. 5,585,033.

[51] Int. Cl.$^6$ .......................... C07D 275/06; C11D 3/48; C09K 15/16

[52] U.S. Cl. .......................... 514/373; 252/405; 548/209; 510/131; 510/161; 510/319

[58] Field of Search .......................... 514/373; 252/405; 548/209; 510/131, 161, 319

[56] References Cited

U.S. PATENT DOCUMENTS

| | | | |
|---|---|---|---|
| 4,188,376 | 2/1980 | Payne et al. | 424/173 |
| 4,382,013 | 5/1983 | Kaneko et al. | 252/354 |
| 4,923,887 | 5/1990 | Bauer et al. | 514/373 |
| 5,276,047 | 1/1994 | Eggensperger et al. | 514/373 |

FOREIGN PATENT DOCUMENTS

| | | |
|---|---|---|
| 1191253 | 8/1970 | United Kingdom . |
| 1330531 | 8/1973 | United Kingdom . |

*Primary Examiner*—Johann Richter
*Assistant Examiner*—Laura R. Cross
*Attorney, Agent, or Firm*—Abelman, Frayne & Schwab

[57] ABSTRACT

Liquid formulations of 1,2-benzisothiazolin-3-one, and methods for making such formulations, are disclosed. Formulations according to the invention contain about 1 to 25 percent by weight 1,2-benzisothiazolin-3-one, about 3 to 7 percent by weight of sodium hydroxide, about 3 to 63 percent by weight of water and about 20 to 65 percent by weight of one or more polyglycol triols having the formula:

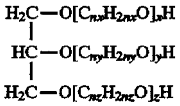

wherein nx, ny and nz are individually selected from the group consisting of 2 and 3, and, when nx, ny and nz are each equal to 2, X+Y+Z has a value equal to or less than about 13.2, and, when nx, ny and nz are each equal to 3, X+Y+Z has a value equal to or less than about 4.45. Formulations exhibiting improved low temperature stability are also prepared by blending of specified co-solvents.

12 Claims, No Drawings

LIQUID FORMULATIONS OF 1,2-BENZISOTHIAZOLIN-3-ONE

This is a divisional of application Ser. No. 08/505,013 filed on Jul. 21, 1995 now U.S. Pat. No. 5,585,033.

FIELD OF THE INVENTION

This invention relates to liquid compositions containing 1,2-benzisothiazolin-3-one and a method for making such compositions, and more particularly to stable liquid compositions containing 1,2-benzisothiazolin-3-one and having low levels of volatile organic compound.

BACKGROUND OF THE INVENTION 1,2-benzisothiazolin-3-one ("BIT") is an effective biocide. It is desirable to provide BIT as a liquid formulation for its intended use. Unfortunately, BIT has low solubility in water. It can be used in the form of an aqueous dispersion; however, BIT tends to settle out from a quiescent mixture, especially at low temperatures.

Liquid formulations of BIT in amines have been disclosed. For example, U.K. Pat. No. 1,191,253 discloses solutions of BIT in water and two or more amine salts. U.K. Pat. No. 1,330,531 discloses solutions of BIT, in the form of its amine salt, in at least one amine and, optionally, water. U.S. Pat. No. 4,923,887 discloses liquid formulations of BIT with ethoxylated (coconut alkyl)-amine, water, alcohols, 1,2-propylene glycol, dipropylene glycol, polyglycols, ether of glycols, or their mixture, as co-solvent. U.S. Pat. No. 5,276,047 discloses liquid formulations of BIT with triamines and triamine mixtures, water, glycols and alkylglycol ethers.

BIT formulations that include amines may not be suitable for certain applications. Amines are typically volatile and have strong unpleasant odors. Amines are generally unacceptable for indirect food contact applications. Amines can cause yellowing of certain water-base latices. The aforementioned amine solutions of BIT may not be suitable for use as biocides for in-can preservation.

U.S. Pat. No. 4,188,376 discloses liquid formulations of alkali metal salts of crude BIT with dipropylene glycol, tripropylene glycol, polyethylene glycols (having a molecular weight of 300), certain alcohols, lower alkyl carbitols and mixtures of the foregoing, with water. Alcohols, lower alkyl carbitols and dipropylene glycol are volatile and are associated with certain odors. Further, BIT formulations containing tripropylene glycol and polypropylene glycol suffer from poor low temperature stability; co-solvents such as propylene glycol or dipropylene glycol must be used to prevent BIT precipitation.

Thus, there is a need for a liquid formulation of BIT that has good stability, even under low temperature storage conditions, has very low volatile organic content ("VOC") content and is suitable for a wide range of applications.

SUMMARY OF INVENTION

An object of the present invention is to provide a liquid formulation of BIT having low VOC.

A second object of the present invention is to provide an amine-free formulation of BIT.

A third object of the present invention is to provide a liquid formulation of BIT which has low VOC and is stable for at least a few weeks at low temperatures, i.e., 0°—10° C.

Liquid formulations of BIT achieving one or more of the aformentioned objects, and methods for making such formulations, are disclosed. Formulations according to the present invention contain 1,2-benzisothiazolin-3-one, sodium hydroxide, water, and polyglycol triols having the formula:

$$\begin{array}{l} H_2C-O[C_{nx}H_{2nx}O]_XH \\ \;\;| \\ HC-O[C_{ny}H_{2ny}O]_YH \\ \;\;| \\ H_2C-O[C_{nz}H_{2nz}O]_ZH \end{array}$$

wherein nx, ny and nz are individually selected from the group consisting of 2 and 3, and, when nx, ny and nz are each equal to 2, X+Y+Z has a value equal to or less than about 13.2, and, when nx, ny and nz are each equal to 3, X+Y+Z has a value equal to or less than about 4.45.

DETAILED DESCRIPTION OF THE INVENTION

Liquid formulations of BIT according to the present invention comprise from about 1 to 25 percent by weight 1,2-benzisothiazolin-3-one, about 3 to 7 percent by weight of solid (non-aqueous) sodium hydroxide, about 3 to 66 percent by weight of water, and about 20 to 65 percent by weight of one or more polyglycol triols having the formula:

$$\begin{array}{l} H_2C-O[C_{nx}H_{2nx}O]_XH \\ \;\;| \\ HC-O[C_{ny}H_{2ny}O]_YH \\ \;\;| \\ H_2C-O[C_{nz}H_{2nz}O]_ZH \end{array}$$

wherein nx, ny and nz are individually selected from the group consisting of 2 and 3, and, when nx, ny and nz are each equal to 2, X+Y+Z has a value equal to or less than about 13.2, and, when nx, ny and nz are each equal to 3, X+Y+Z has a value equal to or less than about 4.45.

When nx, ny and nz are each equal to 2, the polyglycol triol is glycerol ethoxylate. The range for X+Y+Z for glycerol ethoxylate of equal to or less than about 13.2 corresponds to glycerol ethoxylates having an average molecular weight of 700 or less. When nx, ny and nz are each equal to 3, the polyglycol triol is glycerol propoxylate. The range for X+Y+Z for glycerol propoxylate of less than or equal to about 4.45 corresponds to a range of average molecular weight of less than about 350.

While the values of nx, ny and nz are typically the same within a given polyglycol triol, i.e., 2 or 3, this is not required. As stated above, the values nx, ny and nz are individually selected. Also, as stated above, the formulation can include one or more polyglycol triols, i.e., the formulation can be a mixture of glycerol propoxylate and glycerol ethoxylate, as well as either alone. Further, if the formulation contains only glycerol propoxylate, it can be a mixture of glycerol propoxylates having different molecular weights. As used herein, the term "molecular weight" or "average molecular weight" refers to "number average" molecular weight.

Glycerol propoxylate is commercially available from the DOW Chemical Company and Aldrich Company. Glycerol propoxylate having an average molecular weight of 250 is available from DOW Chemical Company under the trademark PT250®. The preparation of polyglycol triols is well known in the art. See, for example, U.S. Pat. Nos. 2,927,918 and 2,990,376.

Glycerol propoxylate having a molecular weight higher than about 350 is not suitable for stabilizing BIT formulations at low temperatures, i.e., 0°–10° C., for extended periods, though it can be used for stabilizing BIT formulations at higher temperatures, i.e., room temperature. Glycerol propoxylate having a molecular weight less than about 250 may result in stable, low temperature formulations; however, the viscosity and VOC of such formulations may be undesirably high. Co-solvents can be used to reduce the viscosity and VOC of such formulations. Thus it is preferable to use glycerol propoxylate having an average molecular weight in the range of about 250 to 350. This range of molecular weight, for glycerol propoxylate, corresponds to a range of values for X+Y+Z of from about 2.72 to 4.45. Currently, it is most preferable to use a glycerol propoxylate having an average molecular weight in the range of 250 to 266 since it is commercially available in this range. This range of molecular weight corresponds to a range of values for X+Y+Z of from 2.72 to 3.00.

The polyglycol triols described above can be used to prepare other low-VOC formulations.

The BIT for use in the present invention can be in its pure form, as a crude product obtained during synthesis or as a moistened powder form.

While solid sodium hydroxide can be used in the present invention, aqueous sodium hydroxide is preferred for ease of use. Aqueous sodium hydroxide having a concentration of at least about 4.3 percent by weight is suitable for use in the present invention. Aqueous sodium hydroxide can be obtained commercially or prepared by mixing solid sodium hydroxide with an appropriate amount of water.

In a preferred embodiment of the present invention, a liquid formulation of BIT comprises from about 15 to 23 percent by weight BIT, about 3 to 7 percent by weight of sodium hydroxide, about 40 to 65 percent by weight of one or more polyglycol triols as defined above, and about 5 to 42 percent by weight of water.

In a currently most preferred embodiment of the present invention, a liquid formulation of BIT comprises about 19.3 percent by weight of BIT, about 6 percent by weight of sodium hydroxide in about 55 percent by weight glycerol propoxylate with average molecular weight 250 to 266 and about 19.7 percent by weight water.

The liquid formulations of BIT according to the present invention are suitable for use as industrial preservatives, for example, in water based paints, adhesives, cleaning agents, emulsions, industrial cooling water or metal working fluids. Such formulations have a much lower VOC content than those of the prior art. Further, some embodiments of liquid formulations of BIT according to the present invention can be stable, i.e., no BIT precipitation, for 6 months or more at 0° C.

Liquid formulations according to the present invention can further comprise a co-solvent which is suitable to reduce the viscosity thereof. It has been observed that, generally, the viscosities of such formulations decrease as the molecular weight of the glycerol propoxylate solvent or glycerol ethoxylate solvent increases. As previously noted, formulations comprising glycerol propoxylates having a molecular weight greater than about 350 are not stable at low temperature. Thus, in one embodiment, glycerol propoxylate having a molecular weight of about 350 or less can be used as the solvent, and a glycerol propoxylate having an average molecular weight less than about 750 but higher than the molecular weight of the solvent glycerol propoxylate can be used as a co-solvent.

It should be understood that if, for example, low temperature stability is required, then the required amount a suitable molecular weight glycerol propoxylate or glycerol ethoxylate, i.e, 20 to 65 weight percent, must be used in the formulation. For example, 2 weight percent of 250 molecular weight glycerol propoxylate and 18 weight percent of 700 molecular weight glycerol propoxylate would not provide a formulation having low temperature stability. At least about 20 weight percent of 250 molecular weight glycerol propoxylate is required. In such a case, any co-solvent polyglycol triol included in the formulation is in addition to the stated requirement for the "solvent" polyglycol triol.

In a further embodiment, glycerol ethoxylate having an appropriate molecular weight can be used as a co-solvent with glycerol propoxylate as the solvent. Likewise, glycerol propoxylate having a suitable molecular weight can be used as a co-solvent with glycerol ethoxylate as the solvent. Co-solvent molecular weight is chosen to result in a lower viscosity for the formulation than would result from using the solvent alone. Co-solvent molecular weight, for a given solvent molecular weight, can be easily determined by the ordinarily skilled artisan.

In another embodiment, the co-solvent can be, without limitation, propylene glycol, dipropylene glycol, dipropylene glycol methyl ether, 2-methyl-1,3-propanediol and polyethylene glycol having a molecular weight of 400 or more. Since some of these co-solvents are volatile, their use may be restricted depending upon the nature of the application.

In one embodiment of the present invention, liquid formulations of BIT can be made in the following manner. BIT is mixed with at least one polyglycol triol. Next, sodium hydroxide and water are added to the mixture. An exothermic reaction will take place causing the temperature of the mixture to rise. If the components of the mixture are contacted at about room temperature, the exotherm will increase the temperature of the mixture to about 35° to 40° C.

In a final step, the mixture is preferably agitated for a period of time sufficient to homogenize the mixture. This step may be carried out with the mixture at the temperature resulting from the aforementioned exotherm, i.e., about 35° to 40° C. Preferably, the mixture is heated to 50° C. and most preferably to 60° C., and maintained at such temperature, for homogenization. If the temperature of the mixture is at least about 50° C., one-half hour should be a sufficient period of time to homogenize the mixture. More time will be required for homogenization at lower temperatures.

In a further embodiment, a co-solvent is added to the mixture. The co-solvent can be added at any step of the aforementioned method.

The present invention is further illustrated by the following non-limiting examples. Unless otherwise indicated, proportions are based on weight. The stability for the formulations described in Examples 1, 2 and 4–7 is expected to have been comparable to that of Example 3. Long term testing, however, was not carried out for these cases.

EXAMPLE 1

19.3 parts of BIT (dried at 110° C. for 1 hour) were added to 55 parts of glycerol propoxylate, average molecular weight 250. The mixture was stirred at ambient temperature to disperse the BIT. 12 parts of 50 % NaOH and 13.7 parts of water were added to the solution and the mixture was stirred for half an hour. The mixture was heated and maintained at 60° C. for one-half hour while stirring. The solution was then filtered at room temperature. The solution was stable for at least 3 weeks at −10° C.

EXAMPLE 2

25 parts of crude BIT paste (equivalent to 19.3 parts of dry BIT) were added to 55 parts of glycerol propoxylate having an average molecular weight of 250. The mixture was stirred at ambient temperature to disperse the BIT. 12 parts of 50% NaOH and 8 parts of water were added to the solution and the mixture was stirred for one-half hour. The mixture was heated and maintained at 60° C. for one-half hour while stirring. The solution was then filtered at room temperature. The solution was stable for at least 3 weeks at −10° C.

EXAMPLE 3

The 55 parts of glycerol propoxylate used in EXAMPLE 2 were replaced by 55 parts of glycerol propoxylate having a molecular weight of 260. The resulting solution had a lower viscosity than the solution of EXAMPLE 2. The solution was stable for more than six months at −10° C.

EXAMPLE 4

The 55 parts of glycerol propoxylate used in EXAMPLE 2 were replaced by 55 parts of glycerol propoxylate having an average molecular weight of 266, The resulting solution had a lower viscosity than the solution of EXAMPLE 2, The solution was stable for at least 1 week at 0° C.

EXAMPLE 5

15 of the 55 parts of glycerol propoxylate used in EXAMPLE 2 were replaced by glycerol propoxylate having an average molecular weight of 266, The resulting solution had a lower viscosity than the solution of EXAMPLE 2, The solution was stable for at least 1 week at 0° C.

EXAMPLE 6

10 of the 55 parts of glycerol propoxylate used in EXAMPLE 2 were replaced by glycerol propoxylate having an average molecular weight of 70.0. The resulting solution has a lower viscosity than the solution of EXAMPLE 2, The solution was stable for at least 2 weeks at 0° C.

EXAMPLE 7

5 of the 55 parts of glycerol propoxylate used in EXAMPLE 2 were replaced by glycerol propoxylate having an average molecular weight of 750. The resulting solution has a lower viscosity than the solution of EXAMPLE 2, The solution was stable for at least 3 weeks at 0° C.

Comparative Example 19.3 parts of dry BIT were added to 55 parts of dipropylene glycol. The mixture was stirred at ambient temperature to disperse the BIT. 12 parts of 50% NaOH and 13.7 parts of water were added to the solution and the mixture was stirred for half an hour. The mixture was then heated and maintained at 60° C. for one-half hour while stirring. The mixture was then filtered.

The formulations prepared according to the Comparative Example and Examples 1 and 3 were tested for VOC content according to a modified ASTM D 2369 method. In the modified procedure, the standard aluminum foil dish used for testing is replaced by a glass dish to avoid any possibility of reaction between aluminum foil and sodium hydroxide. The results at 108° to 113° C. are presented in Table 1 below.

TABLE 1

| | Example 1 | Example 3 | Comp. Example |
|---|---|---|---|
| VOC, % | 3.1 | 1.1 | 47.6 |

We claim:

1. A method of preparing a liquid formulation of 1,2-benzisothiazolin-3-one comprising the steps of:

(a) combining 1,2-benzisothiazolin-3-one with at least one polyglycol triol having the formula:

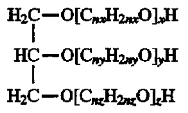

wherein nx, ny and nz are individually selected from the group consisting of 2 and 3, and, when nx, ny and nz are each equal to 2, X+Y+Z has a value equal to or less than about 13.2, and, when nx, ny and nz are each equal to 3, X+Y+Z has a value equal to or less than about 4.45;

(b) adding NaOH and water to the combination of step (a); and (c) agitating the combination of step (b) for a period of time sufficient to homogenize the combination;

wherein the mixture of step (c) contains from about 1 to 25 percent by weight of 1,2-benzisothiazolin-3-one, about 3 to 7 percent by weight of sodium hydroxide, about 20 to 65 percent by weight of the at least one polyglycol triol and about 3 to 63 percent by weight of water.

2. The method of claim 1 wherein during the agitation of step (c) the combination is heated to a temperature of about 50° C.

3. The method of claim 2 wherein the combination is heated for about one-half hour.

4. The method of claim 1 further comprising the step of adding a co-solvent at any step.

5. The method of claim 4 wherein the co-solvent is selected from the group consisting of a glycerol propoxylate having an average molecular weight greater than about 250 and less than about 750, propylene glycol, dipropylene glycol, dipropylene glycol methyl ether, 2-methyl-1,3-propanediol and polyethylene glycol having an average molecular weight greater than about 400.

6. The method of claim 1 wherein nx, ny and nz each equal 3.

7. The method of claim 6 wherein X+Y+Z is in the range of about 2.72 to 3.00.

8. The method of claim 1 where the reaction mixture of step (c) is filtered.

9. The method of claim 1 where the NaOH is in the form of a 50% aqueous solution.

10. The method of claim 1 where the homogenized solution contains by weight percent about 19.3% 1,2-benzisothiazolin-3-one, 6% sodium hydroxide, 19.7% water and 55% glycerol propoxylate having a number average molecular weight in the range of from 250 to 266.

11. A method of preparing a liquid biocide formulation having a VOC of less than about 5% that is stable during storage at temperatures of 0° C. and below that comprises the steps of:

(a) mixing about 19 parts by weight of dry 1,2-benzisothiazolin-3-one with about 55 parts by weight of a polyglycol triol selected from the group consisting of glycerol propoxylate, glycerol ethoxylate, and mixtures thereof;

(b) adding to the mixture of step (a) about 12 parts by weight of 50% sodium hydroxide and about 13 parts by weight of water;

(c) heating the reaction mixture of step (b) to at least 50° C;

(d) stirring the heated reaction mixture for a period of time sufficient to form an homogenized composition; and thereafter (e) filtering the composition of step (d).

12. The biocidal formulation of claim 11 where the polyglycol triol is glycerol propoxylate having a number average molecular weight in the range of from about 250 to about 750.

* * * * *